United States Patent
Auerbach-Nevo et al.

(10) Patent No.: US 11,938,165 B2
(45) Date of Patent: Mar. 26, 2024

(54) STABLE PHARMACEUTICAL FOAM

(71) Applicants: Omrix Biopharmaceuticals Ltd., Rehovot (IL); Ethicon, Inc, Somerville, NJ (US)

(72) Inventors: Tamar Auerbach-Nevo, Rehovot (IL); Ashley Deanglis, Skillman, NJ (US); Israel Nur, Nes Ziona (IL)

(73) Assignees: Omrix Biopharmaceuticals Ltd., Kiryat-Ono (IL); Ethicon, Inc., Raritan, NJ (US)

( * ) Notice: Subject to any disclaimer, the term of this patent is extended or adjusted under 35 U.S.C. 154(b) by 132 days.

(21) Appl. No.: 17/405,491

(22) Filed: Aug. 18, 2021

(65) Prior Publication Data

US 2021/0379140 A1   Dec. 9, 2021

Related U.S. Application Data

(62) Division of application No. 15/700,655, filed on Sep. 11, 2017, now Pat. No. 11,123,397.

(60) Provisional application No. 62/394,371, filed on Sep. 14, 2016.

(30) Foreign Application Priority Data

Sep. 14, 2016  (IL) .......................... 247810

(51) Int. Cl.
| | |
|---|---|
| *A61K 38/01* | (2006.01) |
| *A61K 9/12* | (2006.01) |
| *A61K 38/36* | (2006.01) |
| *A61K 38/48* | (2006.01) |
| *A61L 24/00* | (2006.01) |
| *A61L 24/10* | (2006.01) |
| *A61L 26/00* | (2006.01) |

(52) U.S. Cl.
CPC ............ *A61K 38/018* (2013.01); *A61K 9/122* (2013.01); *A61K 38/014* (2013.01); *A61K 38/363* (2013.01); *A61K 38/4833* (2013.01); *A61L 24/0036* (2013.01); *A61L 24/10* (2013.01); *A61L 26/0028* (2013.01); *A61L 26/0085* (2013.01); *C12Y 304/21005* (2013.01); *A61L 2400/04* (2013.01)

(58) Field of Classification Search
None
See application file for complete search history.

(56) References Cited

U.S. PATENT DOCUMENTS

| | | |
|---|---|---|
| 2,492,458 A | 12/1949 | Bering, Jr. |
| 2,558,395 A | 6/1951 | Studer |
| 6,454,787 B1 | 9/2002 | Maddalo et al. |
| 6,730,299 B1 | 5/2004 | Tayot et al. |
| 8,512,740 B2 | 8/2013 | Delmotte |
| 8,603,543 B2 | 12/2013 | Stucky et al. |
| 8,741,335 B2 | 6/2014 | Mccarthy |
| 8,753,670 B2 | 6/2014 | Delmotte |
| 8,778,883 B2 | 7/2014 | Liao et al. |
| 9,533,069 B2 | 1/2017 | Larsen |
| 9,717,821 B2 | 8/2017 | Schutte et al. |
| 2003/0138391 A1 | 7/2003 | Miller |

FOREIGN PATENT DOCUMENTS

| | | |
|---|---|---|
| CN | 101970021 A | 2/2011 |
| CN | 102014973 A | 4/2011 |
| CN | 105543315 A | 5/2016 |
| EP | 1257304 A1 | 11/2002 |
| JP | 85358982 A | 5/1978 |
| JP | 2014518250 A | 7/2014 |
| JP | 2015535192 A | 12/2015 |
| WO | 2009/144091 A2 | 12/2009 |
| WO | 2010088469 A2 | 8/2010 |
| WO | 2014071053 A2 | 5/2014 |
| WO | 2014086996 A1 | 6/2014 |

OTHER PUBLICATIONS

Jridi, Mourad, et al. "Characterization and potential use of cuttlefish skin gelatin hydrolysates prepared by different microbial proteases." BioMed Research International 2014 (2014). (Year: 2014).*
Garcia, et al., The non-nutritional performance characteristics of peptones made from rendered protein, J Ind. Microbiol. Biotechnology, 2010, pp. 95-102, vol. 37.
Gimenez, et al ., Antioxidant and functional properties of gelatin hydrolysates obtained from skin of sole and squid, Food Chemistry, 2009, pp. 976-983, vol. 114.
Phillips, et al ., "The effects of various milk proteins on the foaming properties of egg white", Food Hydrocolloids, 1989, pp. 163-174, vol. 3 Issue 3.
Razali, et al ., "Antioxidant activity and functional properties of fractionated cobia skin gelatin hydrolysate at different molecular weight", International Food Research Journal, 2015, pp. 651-660, vol. 22 Issue 2.

(Continued)

*Primary Examiner* — Robert J Yamasaki
(74) *Attorney, Agent, or Firm* — David R. Crichton

(57) ABSTRACT

Provided are pharmaceutical foam compositions comprising a peptone, a peptide hydrolysate or an enzymatically-hydrolyzed protein prepared by enzymatic hydrolysis of a full-length protein; methods of preparation and uses thereof.

1 Claim, 7 Drawing Sheets

(56) References Cited

OTHER PUBLICATIONS

Van Der Ven, et al., Correlations between Biochemical Characteristics and Foam-Forming and Stablizing Ability of Whey and Casein Hydrolysates, Journal of Agricultural and Food Chemistry, 2002, pp. 2938-2946, vol. 50 Issue 10.

Van Koningsveld, et al., Formation and Stability of Foam Made with Various Potato Protein Preparations, Journal of Agricultural and Food Chemistry, 2002, pp. 7651-7659, vol. 50 Issue 26.

Walsh, et al., Stablisation of sodium caseinate hydrolysate foams, Food Research International, 2008, pp. 43-52, vol. 41 Issue 1.

* cited by examiner

STABLE PHARMACEUTICAL FOAM

This application is a divisional application of co-pending U.S. patent application Ser. No. 15/700,655 filed on Sep. 11, 2017, which claims priority to U.S. Provisional Patent Application No. 62/394,371 filed on Sep. 14, 2016 and claims benefit of Israel Patent Application 247810 filed Sep. 14, 2016. The complete disclosures of the aforementioned related patent applications are hereby incorporated herein by reference for all purposes.

FIELD OF THE INVENTION

The invention relates to the field of pharmaceutical foams, such as pharmaceutical foams comprising peptones prepared by enzymatic hydrolysis of proteins.

BACKGROUND OF THE INVENTION

A foam is a substance that is formed by dispersing a gas in a liquid, such that bubbles of the gas are trapped in the liquid, with thin films of liquid separating the regions of gas.

Pure liquids comprising no dissolved particles (e.g. 100% $H_2O$) do not foam, such that the addition of a surfactant is generally required in order to reduce the surface tension of the liquid, enabling mixing of the gas with the liquid to form a stable foam. Surfactants are usually amphiphilic in nature (i.e. having both a hydrophilic group and a lipophilic group), with long hydrophobic chains.

Foams prepared from full-length proteins, which act as surfactants, are known. Full-length proteins require denaturation in order to provide the required surfactant characteristics. In order to prepare the foam, an amphiphilic agent is required i.e. a molecule which has both a hydrophilic group and a hydrophilic group, allowing the strands of denatured proteins to form micelles, within which gas, such as air, is trapped. This characteristic allows forming bubbles of air which are stable within the liquid.

Foams are widely used in industry, such as in the food industry or as fire extinguishing foams. Foams are potentially useful in a wide variety of medical and surgical procedures, e.g. for providing protection of a surface, delivery of a drug, or to serve as a barrier for numerous surgical procedures. Use of a liquid foam enables fast and efficient coverage of a large area with a minimal amount of liquid.

For most surgical procedures, it is essential that a foam used must be strong and durable. The strength of a foam may be expressed as the force required for the compression of the foam (i.e. compression strength), which may be measured using a device such as manufactured by Instron or Lloyd, using a method similar to that performed for the determination of the gelatin gel strength, the Bloom number. The Bloom number is a measure of the force (weight in grams) required to compress a given sample area a distance of 4 mm. A higher Bloom number indicates a stronger gel. Bloom number is proportional to the average molecular mass. A low Bloom number (50-125) correlates to an average molecular mass of 20,000-25,000; a medium Bloom number (175-225) correlates to an average molecular mass of 40,000-50,000; while a high Bloom number (225-325) correlates to an average molecular mass of 50,000-100,000.

Background art include U.S. Pat. Nos. 8,778,883; 8,512,740; 8,753,670; 8,741,335; 2,492,458; 6,454,787; 8,603,543; and 6,730,299; PCT Publication Nos. WO 2014/086996; 2014/071053; and 2010/088469; and European Patent No. 1257304.

SUMMARY OF THE INVENTION

The invention, in some aspects thereof, relates to a pharmaceutical (i.e. for medical and/or surgical use) foam composition comprising a peptone prepared by enzymatic hydrolysis of a full-length protein, wherein the foam is free of the full-length protein.

Aspects and embodiments of the invention are described in the specification hereinbelow and in the appended claims.

It is generally known that for gels produced from full-length proteins, the compression force of the gel is directly proportional to the average molecular mass of the protein. This feature of the effect of molecular weight on compression force could be correlated to foams prepared by denatured proteins.

The present Inventors have surprisingly found that peptones, comprising short peptide lengths (e.g. of 90 or fewer amino acids), can be used to produce a stable foam, which has superior qualities, such as higher foam compression strength, as compared to known foams produced from full-length, homogeneous proteins, having higher average molecular mass.

Generally, peptones may be prepared from full-length proteins derived from different sources (e.g. gelatin, casein or protein mixtures) to obtain peptide fragments. Peptide fragments are short chains of amino acid monomers linked by amide bonds. Peptones may be obtained by different methods, such as by enzymatic, acidic, and/or alkali hydrolysis of full-length proteins.

The shortest peptides can be dipeptides, consisting of two amino acids joined by a single peptide bond.

Peptones used in the present invention are water-soluble mixtures comprising peptides and optionally free amino acids, formed by enzymatic hydrolysis/digestion of a full-length protein. In some embodiments, the peptones are devoid of free amino acids.

According to an aspect of the present invention, there is provided a pharmaceutical foam composition comprising a peptone prepared by hydrolysis of a full-length protein, wherein the foam is free of the full-length protein.

According to a further aspect of the present invention, there is provided a pharmaceutical foam composition comprising a peptone prepared by enzymatic hydrolysis of a full-length protein, wherein the foam is free of said full-length protein.

According to a further aspect of the present invention, there is provided a pharmaceutical foam composition comprising a peptone prepared by enzymatic-digestion of a full length protein, wherein the foam is free of the full-length protein.

According to a further aspect of the present invention, there is provided a pharmaceutical foam composition comprising a protein hydrolysate prepared by enzymatic hydrolysis of a full-length protein, wherein said foam is free of the full-length protein.

As used herein, the term "hydrolysate" refers to a material produced by hydrolysis. The term "hydrolysis" usually means the cleavage of chemical bonds by the addition of water. In some embodiments the term "protein hydrolysis" relates to the breakdown of protein into smaller peptides and free amino acids. In some embodiments the term "protein hydrolysis" relates to the breakdown of protein by hydrolysis of the peptide bonds. The term "protein hydrolysate" refers to a product of hydrolysis of a protein that typically comprises peptides and free amino acids.

In the following aspects of the invention, the peptone or the protein hydrolysate comprises enzymatically-digested protein or enzymatically-hydrolyzed protein.

In some embodiments of any of the pharmaceutical foam compositions disclosed herein, the peptone, the protein hydrolysate, or the enzymatically-hydrolyzed protein is devoid of peptides of size greater than 11.7 kDa.

In some embodiments, the peptone, the protein hydrolysate or the enzymatically-hydrolyzed protein comprises peptides of size less than 10.0 kDa.

In some embodiments peptones, protein hydrolysates or enzymatically-hydrolyzed proteins, e.g. peptones or protein hydrolysates or enzymatically-hydrolyzed proteins prepared from gelatin, consist mainly of chain lengths below 10.0 kDa (of approximately 90 or fewer amino acids), such as, for example, from about to 1000 Da up to about 10 kDa, from about 300 Da to about 500 Da, or even below 300 Da.

In one embodiment, the peptone, protein hydrolysate or enzymatically-hydrolyzed protein comprises peptides that are long, continuous, and unbranched peptide chains.

In one embodiment, the peptone, protein hydrolysate or enzymatically-hydrolyzed protein comprises peptides of approximately 90 or fewer amino acids.

In some embodiments, the full-length protein being hydrolyzed is a combination of two or more types of full-length proteins.

In some embodiments, the full-length protein being hydrolyzed is a single type of full-length protein.

In some embodiments, the full-length protein being hydrolyzed is selected from the group consisting of a milk protein (such as casein), a collagen-derived protein (such as gelatin), an egg protein, a blood protein (such as albumin), a yeast protein, a plant protein, or combinations thereof.

In some embodiments, the full-length protein being hydrolyzed is selected from the group consisting of casein and gelatin.

In some embodiments, the foam is stable.

In some embodiments, the enzymatic hydrolysis comprises use of a protease selected from the group consisting of a serine protease, a cysteine protease, a threonine protease, an aspartic protease, a glutamic protease, a metalloprotease and a combination thereof.

In some embodiments, the peptone, protein hydrolysate or enzymatically-hydrolyzed protein is present in the foam at a concentration of higher than about 0.05 to lower than about 20% w/v of the foam, such as, for example, at a concentration of higher than about 1.5 to lower than about 18.0% w/v of the foam, or at a concentration of higher than about 1.66 to lower than about 17.86% w/v of the foam.

In some embodiments, the pharmaceutical foam composition further comprises fibrin and/or fibrinogen, optionally at a concentration in the range of from about 0.1 mg/mL to about 10 mg/mL of the foam, such as, for example, at a concentration in the range of from about 2.3 mg/mL to about 7 mg/mL of the foam.

In some embodiments, the pharmaceutical foam composition further comprises thrombin, optionally at a concentration in the range of from about 0.1 IU/mL to about 100 IU/mL of the foam.

According to a further aspect of the invention, there is provided a method for preparing a pharmaceutical foam composition, comprising a step of: foaming a solution of a peptone, peptide hydrolysate or enzymatically-hydrolyzed protein with a gas, the solution of a peptone, peptide hydrolysate or enzymatically-hydrolyzed protein is prepared by enzymatic hydrolysis of a full-length protein in an aqueous solution, wherein the solution of a peptone, peptide hydrolysate or enzymatically-hydrolyzed protein is free of the full-length protein.

According to a further aspect of the invention, there is provided a method for preparing a pharmaceutical foam composition, comprising a step of: foaming a liquid solution of a peptone, peptide hydrolysate or enzymatically-hydrolyzed protein with a gas, the liquid solution of a peptone or a peptide hydrolysate is prepared by enzymatic hydrolysis of a full-length protein in a liquid, aqueous solution, wherein the solution of a peptone, peptide hydrolysate or enzymatically-hyrolyzed protein is free of the full-length protein.

As used herein, the term "foaming" refers to the process of preparing a foam by mixing a liquid solution with a gas.

Foaming may be achieved manually or automatically. For example, foaming may be achieved by providing two containers (such as two syringes) in fluid communication one with the other, wherein a liquid solution is present in a first of the two containers and a gas, such as air, is present in the second of the two containers; passing the liquid from the first syringe into the gas in the second syringe or the gas from the second syringe into the liquid from the first syringe; then passing the liquid and gas between the two syringes until a foam is achieved.

For example, foaming may be achieved by providing two containers (such as two syringes) in fluid communication one with the other, wherein a liquid for reconstitution is present in a first of the two containers and a gas, such as air, together with a peptone powder or protein hydrolysate is present in the second of the two containers; passing the liquid from the first syringe into the gas in the second syringe or the gas from the second syringe into the liquid from the first syringe; then passing the liquid and gas between the two syringes until a foam is achieved.

Alternatively, a liquid solution may be provided in a sealed container which does not have fluid communication with a gas until an operating mechanism is activated to bring the gas into contact with the liquid. Such a mechanism may include, for example, a pump device or a mechanism for breaking a seal of the sealed container.

In one embodiment, the passing of the liquid between the two syringes is performed at least 6 times.

As used herein, the term "aqueous solution" refers to a solution comprising water and at least one solute dissolved therein. In one embodiment, the term is intended to exclude emulsions or solutions comprising an oil.

An emulsion is a mixture of two or more liquids that are normally immiscible (unmixable or unblendable).

A "liquid" is, for example, a fluid that conforms to the shape of its container but retains a (nearly) constant volume independent of pressure, and/or a flowable material.

In some embodiments, the peptone or peptide hydrolysate comprises enzymatically-digested protein.

Hence, according to an aspect of the present invention, there is provided a method for preparing a pharmaceutical foam composition comprising a step of: foaming a solution of an enzymatically-digested protein with a gas, the solution of a an enzymatically-digested protein prepared by enzymatic hydrolysis of a full-length protein in an aqueous solution, wherein the solution of an enzymatically-digested protein is free of the full-length protein.

Hence, according to an aspect of the present invention, there is provided a method for preparing a pharmaceutical foam composition comprising a step of: foaming a solution of an enzymatically-digested protein with a gas, the solution of a an enzymatically-digested protein prepared by enzymatic hydrolysis of a full-length protein in a liquid aqueous solution, wherein the liquid solution of an enzymatically-digested protein is free of the full-length protein.

In some embodiments of the method disclosed herein, the peptone, the peptide hydrolysate or the enzymatically-digested protein comprises peptides of size less than 10.0 kDa.

In some embodiments, the peptone, the peptide hydrolysate or the enzymatically-digested protein comprises peptides of at least 1000 Da.

In some embodiments, the peptone, the protein hydrolysate or the enzymatically-digested protein comprises peptides having a size in the range of from 1000 Da to less than 10.0 kDa.

In some embodiments, prior to foaming, the solution of a peptone, protein hydrolysate or enzymatically-digested protein is dried and prior to preparation, is reconstituted with a solution comprising water.

In some embodiments, the enzyme hydrolyses the full-length protein to produce a peptone, protein hydrolysate or enzymatically-hydrolyzed protein including peptides of size less than 10.0 kDa.

In some embodiments, the method further comprises, prior to foaming, removing peptides of size greater than 11.7 kDa from the solution of a peptone, protein hydrolysate or enzymatically-hydrolyzed protein.

In some embodiments, the method further comprises, prior to foaming, removing peptides of size greater than 10 kDa from the solution of a peptone, protein hydrolysate or enzymatically-hydrolyzed protein.

In some embodiments, removing peptides of a selected size is performed by filtration, e.g. passage through a size exclusion membrane e.g. in a centrifugal filtration device.

In some embodiments, the full-length protein being hydrolyzed is a combination of proteins, such as 2, 3 or more different full-length proteins.

In some embodiments, the full-length protein being hydrolyzed is a single type of protein.

In some embodiments, the full-length protein being hydrolyzed is casein.

In some embodiments, the full-length protein being hydrolyzed is gelatin.

In some embodiments, enzymatic hydrolysis is carried out with a protease selected from the group consisting of a serine protease, a cysteine protease, a threonine protease, an aspartic protease, a glutamic protease, a metalloprotease and a combination thereof as long as the produced protein hydrolysate or peptone comprises peptides having a size in the range of from 1000 Da to less than 10.0 kDa and/or as long as the foaming ability of the peptone, protein hydrolysate or enzymatically-hydrolyzed protein is not compromised.

Solutions comprising peptone, protein hydrolysate or enzymatically-hydrolyzed protein at a concentration of less than about 50% w/v of the solution are considered to be beneficial for use in preparing the foam as disclosed herein. Hence, in some embodiments, the peptone, protein hydrolysate or enzymatically-hydrolyzed protein is present at a concentration of lower than about 50 w/v of the solution e.g. at a concentration of higher than about 1 to lower than 50% w/v.

In some embodiments, the peptone, protein hydrolysate or enzymatically-hydrolyzed protein is present in the solution at a concentration of higher than about 1 to lower than about 40% w/v, such as, for example, at a concentration of higher than about 5 to lower than about 25% w/v.

In some embodiments, the method further comprises inactivating the enzyme upon completion of the hydrolysis. Enzyme inactivation can be carried out by altering the conditions required for enzymatic activity such as heating and/or pH adjustment, or by removing the enzyme (e.g. by affinity chromatography, size exclusion etc.) as long as the foaming ability of the peptone, protein hydrolysate or enzymatically-hydrolyzed protein is not compromised.

In some embodiments, the peptone, protein hydrolysate or enzymatically-hydrolyzed protein and/or the foam are free of an active enzyme used to prepare the peptone, protein hydrolysate or enzymatically-hydrolyzed protein.

In some embodiments, the method further comprises adding fibrinogen to the solution of a peptone, protein hydrolysate or enzymatically-hydrolyzed protein prior to foaming and after enzyme inactivation, optionally at a concentration in the range of from 1% w/v to up to about 30% w/v of the solution of a peptone, protein hydrolysate or enzymatically-hydrolyzed protein as long as the foaming ability of the peptone, protein hydrolysate or enzymatically-hydrolyzed protein is not compromised.

In some embodiments, the method further comprises adding thrombin to the pharmaceutical foam composition, optionally at a concentration of from about 0.1 IU/mL to about 100 IU/mL of the pharmaceutical foam composition. In one embodiment, the thrombin is added after foaming.

In some embodiments, there is provided a pharmaceutical foam obtained according to any of the methods disclosed herein.

In some embodiments, there is provided the use of the pharmaceutical foam composition disclosed herein, for providing hemostasis, sealing (such as of pleural tissue), anti-adhesion and/or wound healing.

According to an aspect disclosed herein, there is provided a kit comprising a container comprising a peptone, protein hydrolysate or enzymatically-hydrolyzed protein, a device for obtaining a foam and optionally, a full-length protein other than the one subjected to hydrolysis.

In some embodiments, the full-length protein other than the one subjected to hydrolysis is fibrinogen.

In some embodiments, the kit further comprises a container comprising thrombin.

In some embodiments of the kit as disclosed herein, the peptone, protein hydrolysate or enzymatically-hydrolyzed protein comprises peptides of size less than 10.0 kDa.

In one aspect, the invention provides a pharmaceutical foam composition comprising a peptone, protein hydrolysate or enzymatically-hydrolyzed protein prepared by enzymatic hydrolysis of a full-length protein, wherein said foam is free of the full-length protein subjected to hydrolysis.

In some embodiments, the foam as disclosed herein is sturdier and more durable than foams known in the art, having greater tensile strength, determined by its increased resistance to compression.

High strength and durability is important for applications in which the presence of the foam is required over an extended period, such as for wound healing, for sealing procedures or for adhesion prevention. In some situations, hemostasis must be ensured over an extended period of time, for example in patients medicated with anticoagulant drugs. For sealing, the foam is required to have a high strength in order to withstand the stress resulting from specific applications, such as air sealing following lung surgery. For anti-adhesion applications, the durability of the foam is important in order to provide a sturdy physical barrier between different organs at the surgical site. In some embodiments, for wound healing, it is important that a matrix (e.g. foam) in which the cells can grow will remain durable throughout the initial healing phase.

In some embodiments, the foam as disclosed herein has reduced immunogenicity and/or reduced allergenic properties as compared to foams known in the art, allowing for repeated application.

In some embodiments, the foam as disclosed herein has greater adhesiveness than foams known in the art, which is highly advantageous in certain medical applications to allow the material to remain in position at the site of application. For example, in some embodiments, the foam as disclosed herein has a mean adhesion force to tissue of greater than 1 N/inch$^2$, such as, for example at least 1 N/inch$^2$, at least 2 N/inch$^2$, at least 3 N/inch$^2$, at least 4 N/inch$^2$, at least 5 N/inch$^2$, or even at least 6 N/inch$^2$. In some embodiments, the mean adhesion force to tissue is in the range of from about 1 N/inch$^2$ to about 6 N/inch$^2$.

In some embodiments, the foam as disclosed herein has greater stiffness than foams known in the art, which is highly advantageous in certain medical applications i.e. for application to tissues where the foam must have strong cohesion to seal fluid or air leaks, especially where pressures may be elevated. For example, in some embodiments, the foam as disclosed herein has a mean stiffness of at least 3 N/mm, such as, for example, 3 N/mm, 4 N/mm, at least 5 N/mm at least 6 N/mm, at least 7 N/mm, at least 8 N/mm, at least 9 N/mm, at least 10 N·mm, at least 11 N/mm, at least 12 N/mm, at least 13 N/mm, at least 14 N/mm, at least 15 N/mm, at least 16 N/mm, at least 17 N/mm, or even at least 18 N/mm. In some embodiments the mean stiffness is in the range of from about 3 N/mm to about 19 N/mm. Additionally, in some embodiments, the foam must be able to remain intact, if the underlying tissue is expanding or contracting.

In some embodiments, the foam is stable, is not transient, and e.g. maintains its foam structure including height, volume, and/or porosity/mean pore size, for at least one hour after formation.

As used herein, the term "stable" with regard to a foam (e.g. a non-dried foam) relates to a foam that can substantially support its own structure without collapse at a specified temperature. For example, foam which is stable in vitro at physiological temperature retains at least 80% (such as 90%, 95% or higher) of its original structure including height, volume, and/or porosity/mean pore size for at least 1 hour at ambient temperature. Typically, collapse is most evidently characterized by the loss of foam structure after foam formation. Collapse usually results in a structure whose volume is significantly smaller than the volume of the original prepared foam.

In some embodiments, the foam as disclosed herein has a faster in-vivo degradation time than foams known in the art. Since peptones are already partially degraded proteins, these can be completely degraded more rapidly than native, intact/folded proteins. This property may reduce one or more of inflammatory reaction, foreign body reaction and post-surgical adhesions.

As used herein, the term "degradation time" means the time required for at least 90% of the peptone components of the foam to be degraded in-vivo.

The desired degradation time of the foam is dependent on the intended use (e.g. as sealant or hemostat), tissue type, amount used, chance of re-bleeding or re-leaking, pressures involved, patient condition, etc. In general, it is desired that a sealant or hemostat be present long enough to allow for tissue repair, but to not impede tissue repair. For example, in some embodiments, it is preferred that a foam for use as a sealant or hemostat has a longevity of 4-5 days.

In some embodiments, the foam as disclosed herein is free of a non-protein surfactant.

In some embodiments, the foam as disclosed herein is prepared in the absence of a non-protein surfactant.

In some embodiments, the peptone, protein hydrolysate or enzymatically-hydrolyzed protein used to prepare the foam (i.e. prior to foaming) has not being subjected to denaturation prior to foaming.

In some embodiments of the invention, the peptone is not denatured.

In some embodiments the full-length protein subjected to hydrolysis, to prepare the peptone, the protein hydrolysate or enzymatically-hydrolyzed protein has not been subjected to denaturation prior to foaming.

In some embodiment the solution of a peptone, protein hydrolysate or enzymatically-hydrolyzed protein is free from denatured proteins.

In some embodiments the solution of a peptone, peptide hydrolysate or enzymatically-hydrolyzed protein is free from denatured proteins other than the hydrolyzing enzyme(s).

In some embodiment the solution of a peptone, peptide hydrolysate or enzymatically-hydrolyzed protein includes other full-length protein, wherein the other full length protein is one that was not subjected to the enzymatic hydrolysis In some embodiments, the other full length protein is present in the peptone, protein hydrolysate or enzymatically-hydrolyzed protein in addition to the hydrolyzing enzyme, and the other full-length protein has not been subjected to denaturation prior to foaming.

Typically, denaturation is a process of modifying the secondary and/or tertiary molecular structure of a protein/peptide e.g. by heating, by treatment with alkali, acid, urea, or detergent. When a protein is denatured, secondary and/or tertiary structures are altered but the peptide bonds of the primary structure between the amino acids are left intact.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

As used herein, the indefinite articles "a" and "an" mean "at least one" or "one or more" unless the context clearly dictates otherwise.

As used herein the term "about" refers to ±10%.

Unless otherwise defined, all technical and scientific terms used herein have the same meaning as commonly understood by one of ordinary skill in the art to which the invention pertains. In addition, the descriptions, materials, methods, and examples are illustrative only and not intended to be limiting. Methods and materials similar or equivalent to those described herein can be used in the practices of the present invention.

As used herein, the term "enzymatic hydrolysis" means a full-length protein is enzymatically hydrolyzed to a point at which the peptone solution is free of the original full-length protein.

In one embodiment, enzymatic hydrolysis according to the invention also includes hydrolyzation to a point in which a given enzyme did not hydrolyze/digest all possible digestion sites of the full length protein that are recognized by the enzyme.

In some embodiments, the pharmaceutical foam composition disclosed herein is substantially devoid and/or substantially free of the full-length protein that was subjected to enzymatic hydrolysis. As used herein, the term "substantially free" or "substantially devoid of" with regard to the full-length protein means that the composition contains less than 5 w/v %, less than 4 w/v %, less than 3 w/v %, less than 2 w/v %, less than 1 w/v %, less than 0.5 w/v %, less than 0.1 w/v % or less than 0.05 w/v% of the full-length protein.

As used herein, the term "solution of a peptone" refers to a solution, such as a liquid solution, comprising a peptone and optionally other components, such as small molecules, salts, active pharmaceutical ingredients, and coagulation factors.

As used herein, the term "solution of a peptide hydrolysate" refers to a solution, such as a liquid solution, comprising the peptide hydrolysate and optionally other components, such as small molecules, salts, active pharmaceutical ingredients, and coagulation factors.

As used herein, the term "solution of an enzymatically-hydrolyzed protein" refers to a solution, such as a liquid solution, comprising the enzymatically-hydrolyzed protein and optionally other components, such as small molecules, salts, active pharmaceutical ingredients, and coagulation factors.

In some embodiments, the peptone is derived from a milk protein (such as casein), a collagen-derived protein (such as gelatin, e.g., prepared from skin, cartilage or bones), an egg protein, a blood protein (such as albumin), a yeast protein, a plant protein, or combinations thereof.

In addition to containing small peptides, the resulting peptone solution may also include fats, metals, salts, vitamins and many other biological compounds.

According to an aspect, the invention provides a kit comprising a container comprising a protein hydrolysate prepared by enzymatic hydrolysis of a full-length protein, a device for foaming the hydrolysate and optionally, a full-length protein other than that subjected to the enzymatic hydrolysis.

According to a further aspect, the invention provides a method for preparing a pharmaceutical foam composition, comprising a step of: foaming a solution of a protein hydrolysate with a gas, the solution of the protein hydrolysate prepared by enzymatic hydrolysis of a full-length protein in an aqueous solution, wherein said solution is free of said full-length protein.

Yet, according to a further aspect, the invention provides a method for preparing a pharmaceutical foam composition comprising: enzymatically hydrolyzing a full-length protein in an aqueous solution until said solution is free of said full-length protein thereby obtaining a solution of a peptone or protein hydrolysate; and foaming said solution of said peptone or protein hydrolysate with a gas.

In another aspect, the invention provides a pharmaceutical foam composition obtained according to the method of the invention.

According to an aspect of the present invention, there is provided a peptone-based foam prepared by hydrolysis of a full-length protein, wherein the foam is free of the full-length protein that was subjected to hydrolysis.

The term "peptone based foam" means that the majority of the foam (more than half of the total weight of the foam) is composed of peptone.

Other components such as fibrinogen, fibrin, thrombin, etc. may also be present in the foam e.g. proteins other than the full-length protein that was subjected to hydrolysis can be present. For example the foam can comprise 1% to 100% peptone out of the total dissolved components.

Proteins other than the full-length protein that was subjected to hydrolysis can be present in the foam in at concentrations of up to or equal to 49% while the remaining components consist of peptone.

As used herein, the term "full-length" protein refers to a protein prior to hydrolysis/digestion.

In some embodiments, the ratio of air to liquid used in preparing the foam was in the range of from 1:3 to 3:1 air:liquid. In some preferred embodiments, the ratio of air to liquid is in the range of from about 2:1 to about 3:1 air:liquid.

Protein molecules are often very large and are made up of hundreds to thousands of amino acid units. Proteins include naturally occurring proteins or fragments thereof and/or synthetic proteins.

The foam can be dried or non-dried. A dry foam can be obtained by reducing the concentration of water e.g. by air drying, vacuum drying, or freeze drying.

The term "dry foam" refers to foam comprising water content of equal to or less than 3% by weight based on the total weight of the foam composition (w/w).

According to an aspect of the present invention, there is provided a method for promoting blood coagulation; sealing; prevention and/or reduction of adhesion; and/or wound healing comprising application of a pharmaceutical foam composition according to the invention.

All aspects and embodiments relating to peptone described herein above and below also intend to relate to "peptide hydrolysate" or "enzymatically-hydrolyzed protein", where applicable.

BRIEF DESCRIPTION OF THE DRAWINGS

Some embodiments of the invention are described herein with reference to the accompanying figures. The description, together with the figures, makes apparent to a person having ordinary skill in the art how some embodiments of the invention may to be practiced. The figures are for the purpose of illustrative discussion and no attempt is made to show structural details of an embodiment in more detail than is necessary for a fundamental understanding of the invention. For the sake of clarity, some objects depicted in the figures are not to scale.

In the Figures.

DESCRIPTION OF SOME EMBODIMENTS OF THE INVENTION

Figure 1:
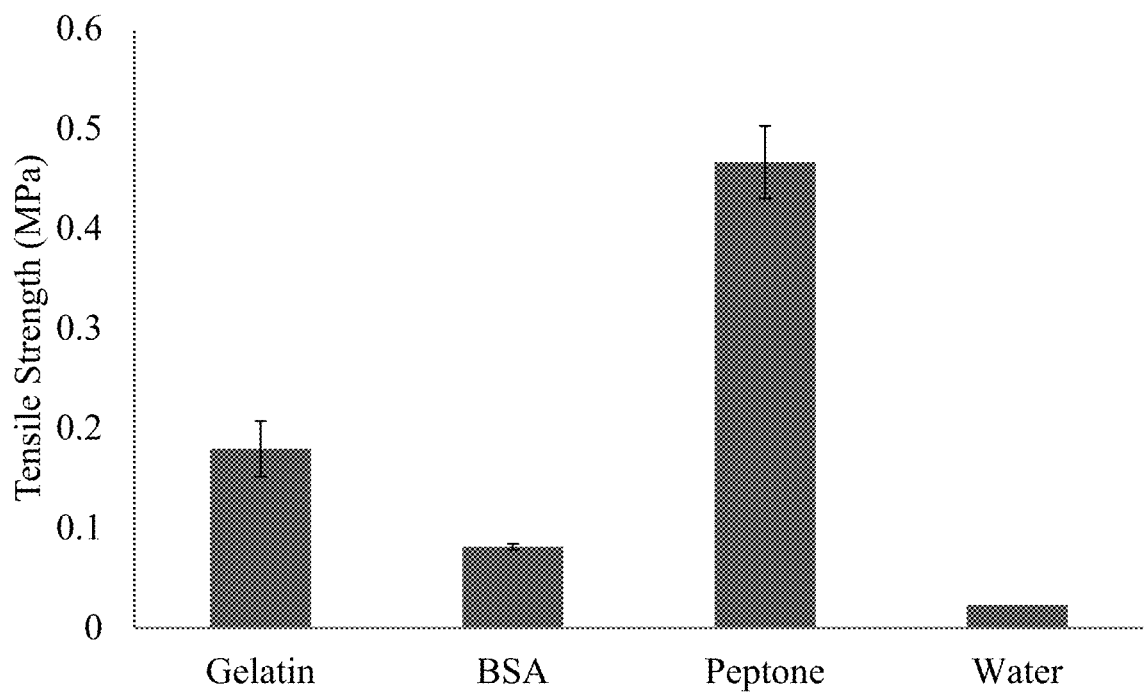
FIG. 1 is a bar graph showing the tensile strength of foams prepared from full-length gelatin and full-length Bovine Serum Albumin (BSA), or from peptone obtained by enzymatic hydrolysis of full-length gelatin.

The invention, in some embodiments thereof, relates to a pharmaceutical foam composition comprising peptone prepared by enzymatic hydrolysis of protein(s).

The principles, uses and implementations of the teachings herein may be better understood with reference to the accompanying description. Upon perusal of the description, one skilled in the art is able to implement the invention without undue effort or experimentation.

Before explaining at least one embodiment in detail, it is to be understood that the invention is not necessarily limited in its application to the details of construction and the arrangement of the components and/or methods set forth in the following description. The invention is capable of other embodiments or of being practiced or carried out in various ways.

The phraseology and terminology employed herein are for descriptive purpose and should not be regarded as limiting.

As shown in the Examples presented below, it was surprisingly found that greater force was required to compress foams obtained from peptones as compared to foams prepared from full-length proteins.

Further, unexpectedly, only peptones resulting from enzymatic hydrolysis, and not from acid hydrolysis, were shown to yield durable foams.

In ex-vivo experiments it was further shown that foams obtained from peptones have increased adhesive characteristics as compared to foams obtained from full-length proteins.

It was further surprisingly found that the presence of cross-linker was not required to obtain sturdy foam from peptones, but can be optionally be added.

Further surprisingly, it was found that peptones comprising peptides of equal to or less than 10 kDa provided sturdier foams than full-length proteins.

EXAMPLES

Materials and Methods
Materials
 BSA (Sigma, cat #A7030)
 Gelatin from porcine skin (Sigma, cat #G1890)
 Peptone obtained by enzymatic hydrolysis of gelatin (Sigma, cat #70951)
 Casein (Sigma, cat #C3400)
 Peptone obtained by enzymatic hydrolysis of casein (Sigma, cat #70172)
 Peptone obtained by acidic hydrolysis of casein (Sigma, cat #70171)
 BAC2 component of EVICEL®, cats #3901, 3902, 3905, Ethicon)

Thrombin (Thrombin component of EVICEL®, cats #3901,3902, 3905, Ethicon)

Water for preparation and dilution of solutions was deionized water.

Compression tests were performed using a Lloyd LF Plus device, with a 10 mm, flat bottom stencil, or an Instron.

Example 1

Tensile Strength of Foams Prepared from Peptone and from Full-Length BSA and Gelatin The force required for the compression of each of the following foams was measured:
1. Foam comprising full-length gelatin, fibrinogen source (BAC2) and thrombin;
2. Foam comprising BSA, fibrinogen source (BAC2) and thrombin;
3. Foam comprising peptone obtained by enzymatic hydrolysis of full-length gelatin, fibrinogen source (BAC2) and thrombin; and
4. Control foam comprising fibrinogen source (BAC2) and thrombin.

A 5% w/v aqueous solution of each of full-length gelatin, full-length BSA and peptone obtained by enzymatic hydrolysis of full-length gelatin was prepared (foam nos. 1-3 from left to right). To 5 mL of each solution, 500 μL of a concentrated BAC2 solution were added to provide a final concentration of 10% BAC2, comprising in to total about 35 mg fibrinogen. For control foam (no. 4), 5 mL water were added to 500 μL concentrated BAC2 solution.

The solutions were foamed by using two syringes, interconnected with a 2 cm Tyvec tubing (~2 mm diameter). The solutions as prepared above were drawn into the first syringe, and 10 mL of air were drawn into the second syringe. The solutions were expelled back and forth between the first and second syringes, thereby admixing the solution with the air.

At the final step of the preparation, 20 IU Thrombin in 40 mM $CaCl_2$ in a volume of 200 μl were added to the foam by adding the thrombin solution to one syringe and expelling the foam back and forth one more time. The prepared foam was expelled to rim height into a well of a 24-tissue culture plate. The foam was allowed to stand for one hour at room temperature. The force required for compression was then evaluated using a 10 $mm^2$ stencil, pressing at a rate of 5 mm/min for a total length of 12 mm in triplicate. The results were recorded and analyzed.

As seen in FIG. 1, it was surprisingly found that foam prepared from the peptone obtained by enzymatic hydrolysis of full-length gelatin required the highest force for compression of the foam. As shown by the control sample (Water), the force required for compression of BAC2 alone was negligible. Furthermore, full-length BSA (66.5 kDa), a globular protein, was shown to require smaller force for compression than that required for gelatin.

Example 2

Tensile Strength of Foams Prepared from Peptone Obtained by Enzymatic or Acid Hydrolysis of Selected Full-Length Proteins In order to study the effect of different hydrolysis mechanisms by which peptones were obtained from full-length proteins on the compression force, the force required for compression of foams prepared from an aqueous solution of peptones obtained by enzymatic or acid hydrolysis of casein was measured. For further comparison, the force required for compression of foams obtained from full-length gelatin, BSA and casein were also measured.

A 5% w/v aqueous solution of each of full-length gelatin, BSA and casein; peptone obtained by enzymatic or acidic hydrolysis of casein; and peptone obtained by enzymatic hydrolysis of gelatin was prepared. Foam was prepared in two 50 mL syringes. The first syringe was loaded with 20 mL of a 5% protein solution and 2 mL BAC2. In the second syringe 40 mL air were loaded. Following foaming by vigorous admixing of the air into the liquid the prepared material was expelled into a cup with a diameter of 60 mm, at a height of 20 mm.

The force required for compression was evaluated at 0.5 mm/sec for a depth of 4 mm. Foams prepared from full-length gelatin and peptones were tested in triplicate, foams prepared from full-length BSA and casein were tested in duplicate.

Figure 2:
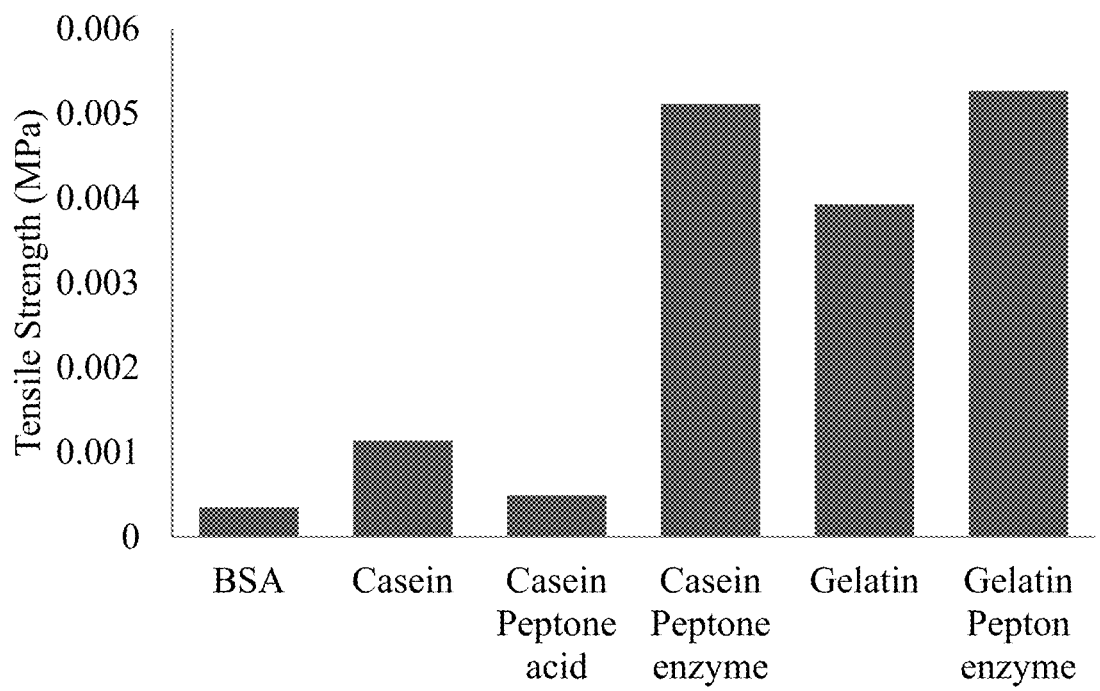
FIG. 2 is a bar graph showing the tensile strengths of foams prepared from full-length BSA, casein or gelatin and from peptone obtained by enzymatic or acid hydrolysis of the full-length casein or gelatin.

Results are presented in FIG. 2.

As shown in FIG. 2, the force required for compression of the foam prepared from peptone obtained by enzymatic hydrolysis of casein or gelatin was significantly higher than that of foam prepared from the respective full-length proteins, indicating a reverse correlation between the chain length and the compression force required. In contrast, foam prepared from peptone obtained by acid hydrolysis of casein was found to be less stable upon compression than foam prepared from full-length casein. It was further noted that very similar results were seen with foams prepared from peptones obtained from gelatin and from casein.

Example 3

Effect of Peptone Concentration on Tensile Strength of Foam

A 50% w/v aqueous solution of peptone obtained by enzymatic hydrolysis of full-length gelatin was prepared by dissolving 50 g peptone powder in 100 mL water. The solution was diluted with water to obtain 1%, 5%, 10%, and 25% aqueous solutions of peptone.

5 mL of each solution was foamed as described in Example 1.

Figure 3:
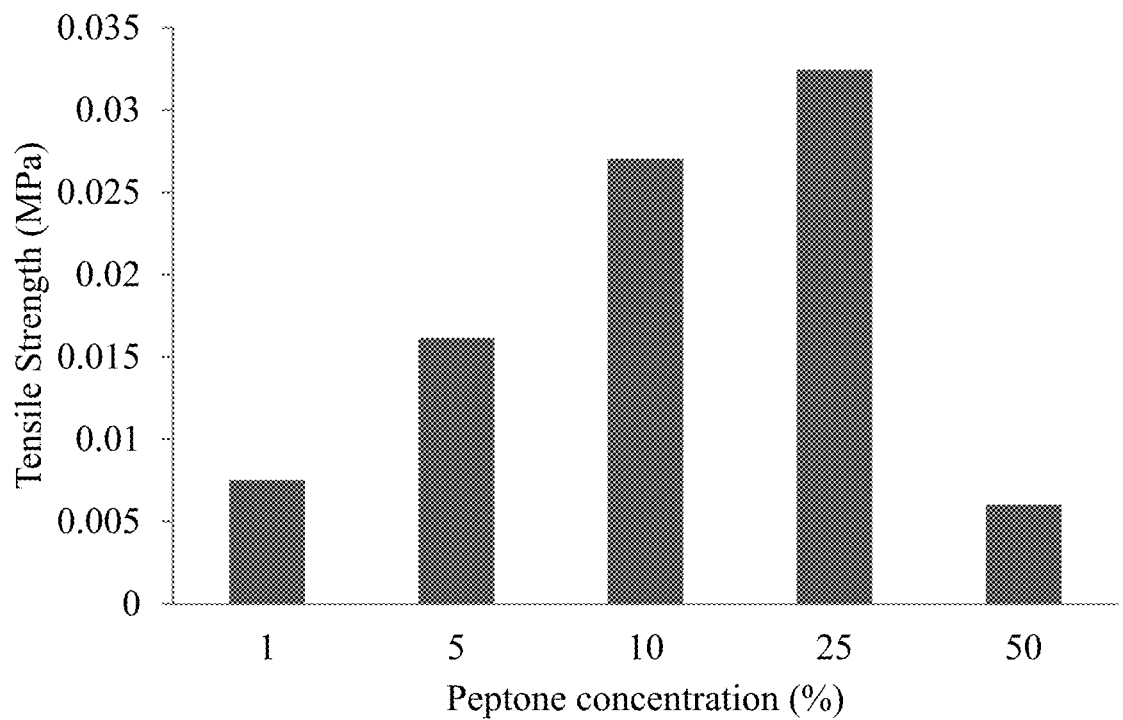
FIG. 3 is a bar graph showing the effect of peptone concentration on tensile strength for peptone obtained by enzymatic hydrolysis of full-length gelatin.

At the final step of the preparation, 200 µL of a 100 IU/mL Thrombin solution in 40 mM $CaCl_2$ were added to the foam, and the final foam prepared and the force required for compression tested in quadruplicate, substantially as described in Example 1 above, except that pressing to a depth of 4 mm (instead of 12 mm) at 5 mm/sec was performed. Results are presented in FIG. 3.

The results show that for foam comprising a concentration of between 1 to 25% peptone w/v in water, the force required for compression was directly proportional to the peptone concentration. Peptone concentrations of equal to or greater than 50% w/v resulted in reduced foam quality as reflected in the lower force required for compression.

Example 4

Effect of BAC2 Concentration on Tensile Strength of Foam

A 5% aqueous solution of peptone obtained by enzymatic hydrolysis of gelatin was prepared.

Four samples, each comprising 5 mL peptone solution were prepared. Each sample was foamed as described in Example 1.

Figure 4:
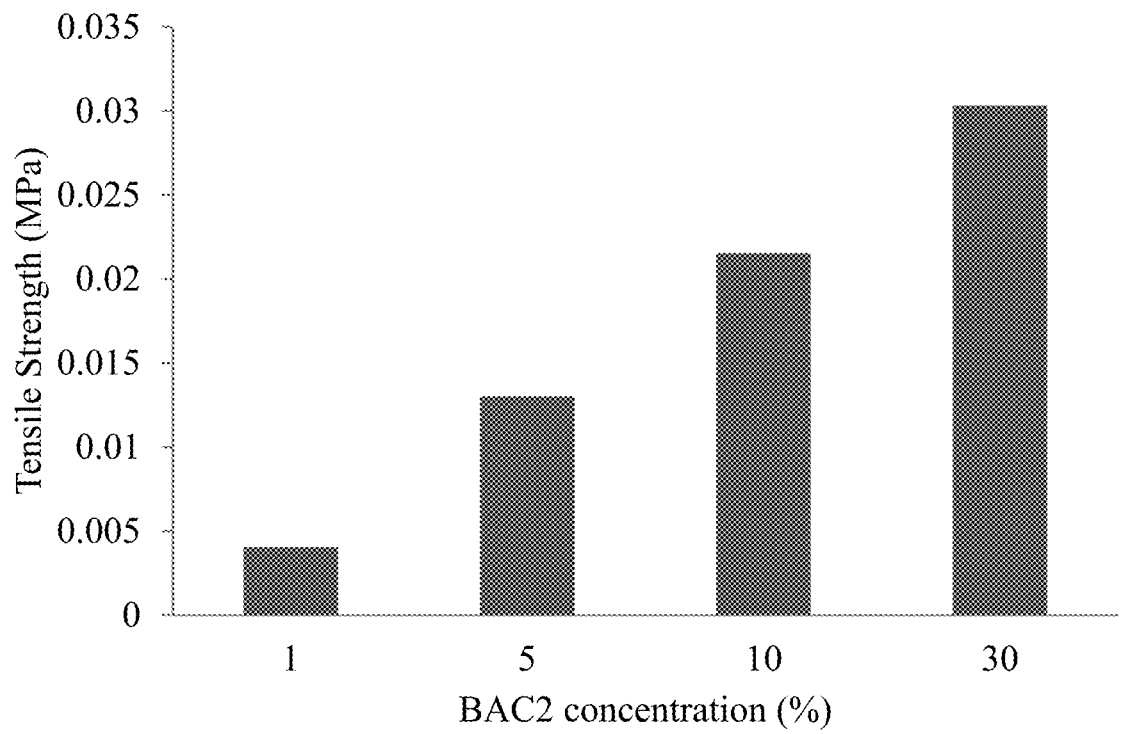
FIG. 4 is a bar graph showing the effect of BAC2 concentration on tensile strength for peptone obtained by enzymatic hydrolysis of full-length gelatin.

At the final step of the preparation, BAC2, at concentration of 1%, 5%, 10% or 30% w/v was added, wherein each percent of BAC2 comprised about 7 mg fibrinogen. The, final foam was prepared and tested in quadruplicates as described in Example 3. Results are presented in FIG. 4.

The results show that for foam comprising a concentration of between 1 to 30% BAC2, the force required for compression was directly proportional to the peptone concentration.

Example 5

Tensile Strength of Foams Prepared from Peptone and from Gelatin in the Presence and Absence of Fibrinogen In order to test for the requirement of a protein cross-linker, the tensile strength of foams prepared from 5% w/v aqueous solution of each of full-length gelatin, and peptone obtained by enzymatic hydrolysis of full-length gelatin, in the presence and absence of fibrinogen (provided by BAC2), were measured. Results are presented in FIG. 5.

Foams were prepared substantially as described in Example 1, except that foams comprising about 35 mg fibrinogen and 20 IU thrombin, as well as foams devoid of BAC2 were prepared. Triplicates of the samples were tested.

Figure 5:
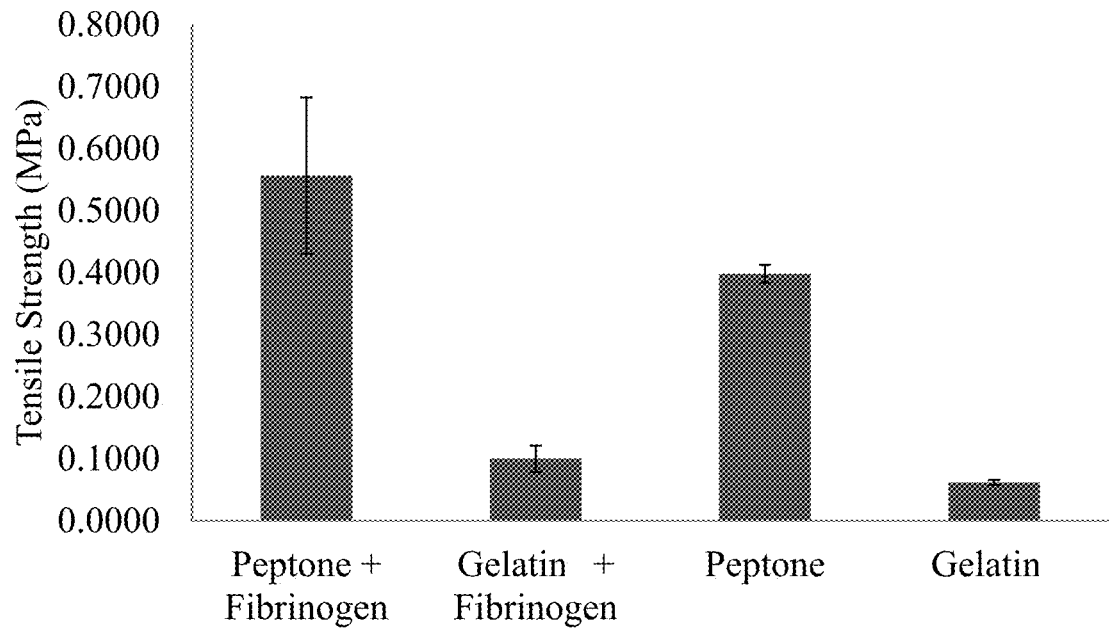
FIG. 5 is a bar graph showing the tensile strength of foams prepared from full-length gelatin and from peptone derived from enzymatic hydrolysis of full-length gelatin in the presence and absence of fibrinogen.

As shown in FIG. 5, the increased force required for compression of foams prepared from peptone obtained by enzymatic hydrolysis of full-length gelatin as compared to those prepared from full-length gelatin was observed in both the presence and absence of fibrinogen provided by BAC2.

Use of an alternative cross-linker, 4-armed PEG was also tested. However, foams cross-linked with the 4-armed PEG showed breakdown of the foam, which could therefore not be evaluated.

Example 6

Tissue Adhesion

Aqueous solutions were prepared as follows:

5% w/v full-length albumin+30 mg/mL concentrated BAC2+2 IU/mL EVICEL® Thrombin (1:3 ratio of liquid:air);

5% w/v peptone obtained by enzymatic hydrolysis of gelatin+30 mg/mL concentrated BAC2+3 IU/mL EVICEL® Thrombin (1:3 ratio of liquid:air); and 5% w/v peptone obtained by enzymatic hydrolysis of casein+30 mg/mL concentrated BAC2+10 IU/mL EVICEL® Thrombin (1:3 ratio of liquid:air).

Foams were prepared from 5 mL of each solution, substantially as described above for Example 1, except that the amount of BAC2 added to each foam was identical, and the amount of thrombin was adjusted to achieve a comparable fibrinogen polymerization rate.

Five replicates were tested for each formulation. The liquid:air ratio for each foam preparation was 1:3, providing a homogeneous foam, without large air pockets or bubbles.

Foams were tested for adhesion to tissue using ASTM F2258 (Standard Test Method for Strength Properties of Tissue Adhesives in Tension). Freshly harvested porcine pleura, as a tissue substrate, was mounted on 1 inch×1 inch plates secured to the load cell and bottom grip of an INSTRON® (Tensile Tester model 5565 with 10N Load Cell) device for tensile strength measurement. The crosshead and load cell were lowered to ensure alignment of the two tissue surfaces. A 3 mm gap between the tissue surfaces was maintained for each sample.

Before expressing the foam, the crosshead was moved away from the bottom. Each formulation was prepared immediately before testing and approximately 3 mL of formulation was expelled on the tissue surface for each sample. Excess material was wiped away from the perimeter of the fixture immediately after the top plate was returned to the initial gap height. A 15-minute time period was allowed for complete polymerization of the foam before testing. The cross head moved in a vertical direction at 5 mm/min until the test was stopped. The load-extension output for each sample was recorded by the INSTRON® control software. The peak adhesive force, stiffness and failure mode was recorded for each sample. Tissue adhesion results are presented in FIG. 6. Stiffness (material strength) results are presented in FIG. 7.

Figure 6:
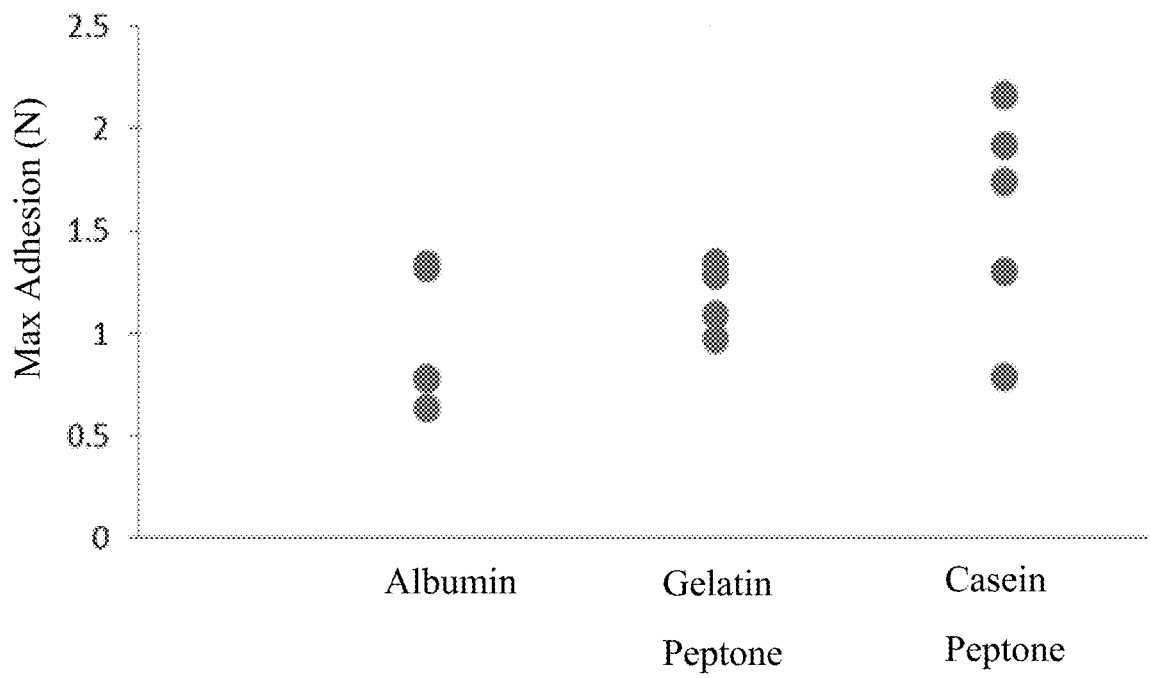
FIG. 6 is a dot graph showing tissue adhesion strength of foams prepared from peptones obtained by enzymatic hydrolysis of full-length gelatin or casein, as compared to foams prepared from full-length albumin.
Figure 7:
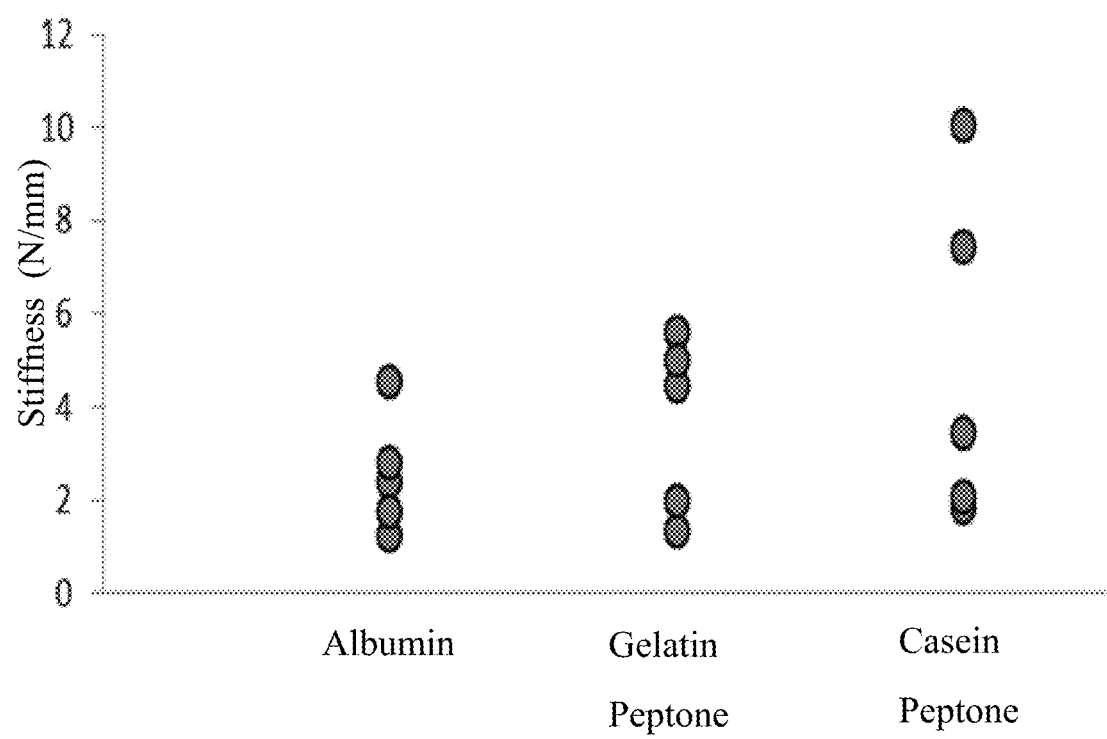
FIG. 7 is a dot graph showing stiffness of foams prepared from peptones obtained by enzymatic hydrolysis of full-length gelatin or casein, as compared to foams prepared from full-length albumin.

As seen in FIGS. 6 and 7, tissue adhesion was greater with foams prepared from gelatin peptone or casein peptone as compared to intact albumin. Foams prepared from casein peptone had the highest maximum adhesion and stiffness. Mean maximum adhesion scores were as follows: intact albumin 0.97 N; gelatin peptone 1.19 N; and casein peptone 1.58 N.

For all formulations, the failure mode was adhesive, i.e. failure occurred at the tissue: foam interface, and not cohesive i.e. failure did not occur within the test article.

Example 7

Scanning Electron Microscope (SEM) Studies

Foams were prepared from aqueous solutions of 5% w/v full-length gelatin and 5% w/v peptone obtained by enzymatic hydrolysis of full-length gelatin, with the addition of BAC2 and thrombin, as described above for Example 1.

Figure 8A:
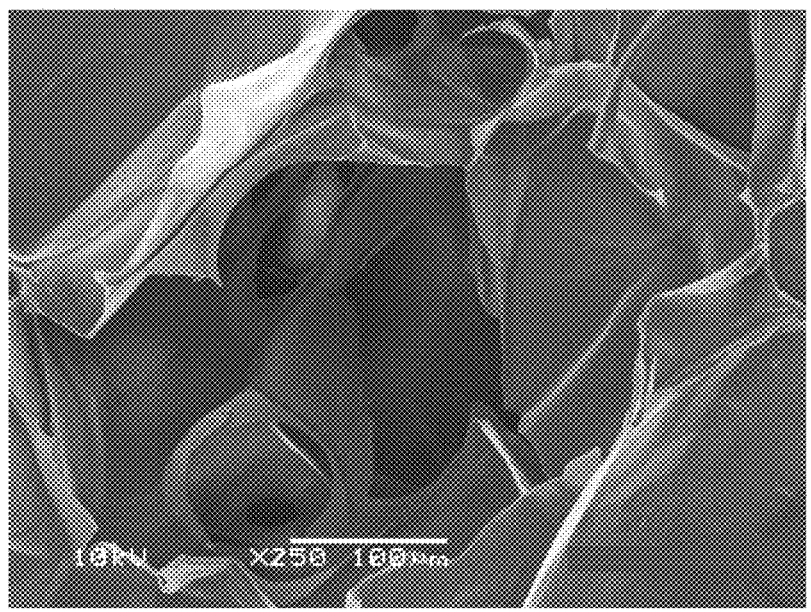
FIG. 8A shows scanning electron micrographs for foams prepared from full-length gelatin.
Figure 8B:
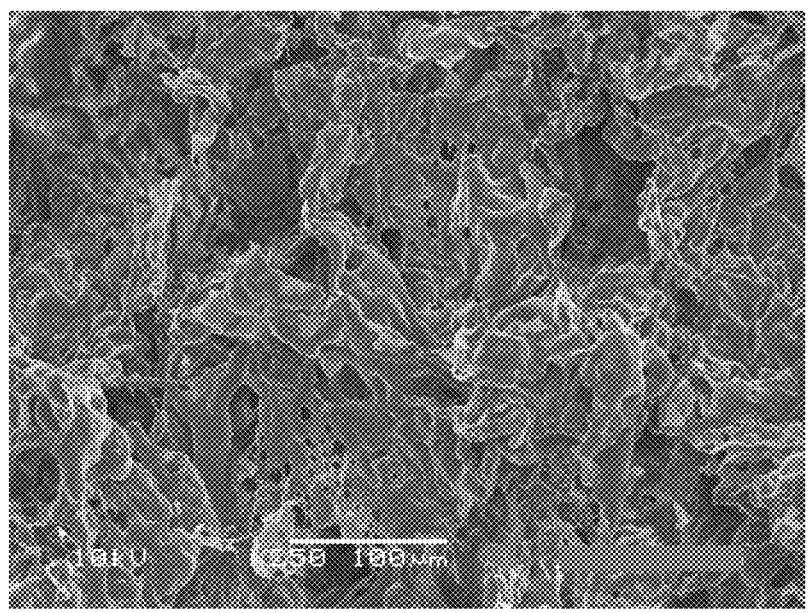
FIG. 8B shows scanning electron micrographs from foam prepared from peptone obtained by enzymatic hydrolysis of full-length gelatin.

FIGS. 8A and 8B show electron micrographs for foams prepared from full-length gelatin (8A) and from foam prepared from peptone obtained by enzymatic hydrolysis of gelatin (8B).

As seen in FIGS. 8A and 8B, foams prepared from peptone had higher density and smaller air pockets than foam prepared from full-length protein. It is expected that the foam prepared from gelatin would be less stable due to the large bubble structure, while the foam obtained from the peptone would be more stable and more rigid. It is hypothesized that the differences may be due to the greater hydrophobicity of the full-length protein.

Example 8

Effect of Peptide Size on Tensile Strength

In order to investigate the effect of peptide size on tensile strength, aqueous solutions of 5% w/v full-length gelatin and 5% w/v of peptone obtained by enzymatic hydrolysis of full-length gelatin were prepared.

10 mL of the solution comprising the peptide was subjected to centrifugation through a Amicon Ultra centrifugal filters, Ultra-15 with a 10 kDA cut-off centrifugation filter in a centrifugal filtration device (Sigma, Z706345). The device was subjected to 3500 G centrifugal force for 10 minutes at room temperature, ensuring that the filtered solution included only peptides with a length of less than 10 kDa.

Foams were prepared from 5 mL of each of the full-length gelatin solution, and of the solutions comprising peptone, with and without filtration centrifugation, as described in Example 1. Force required for compression of the foams was tested in quadruplicates as described in Example 1. Results are presented in FIG. 9.

Figure 9:
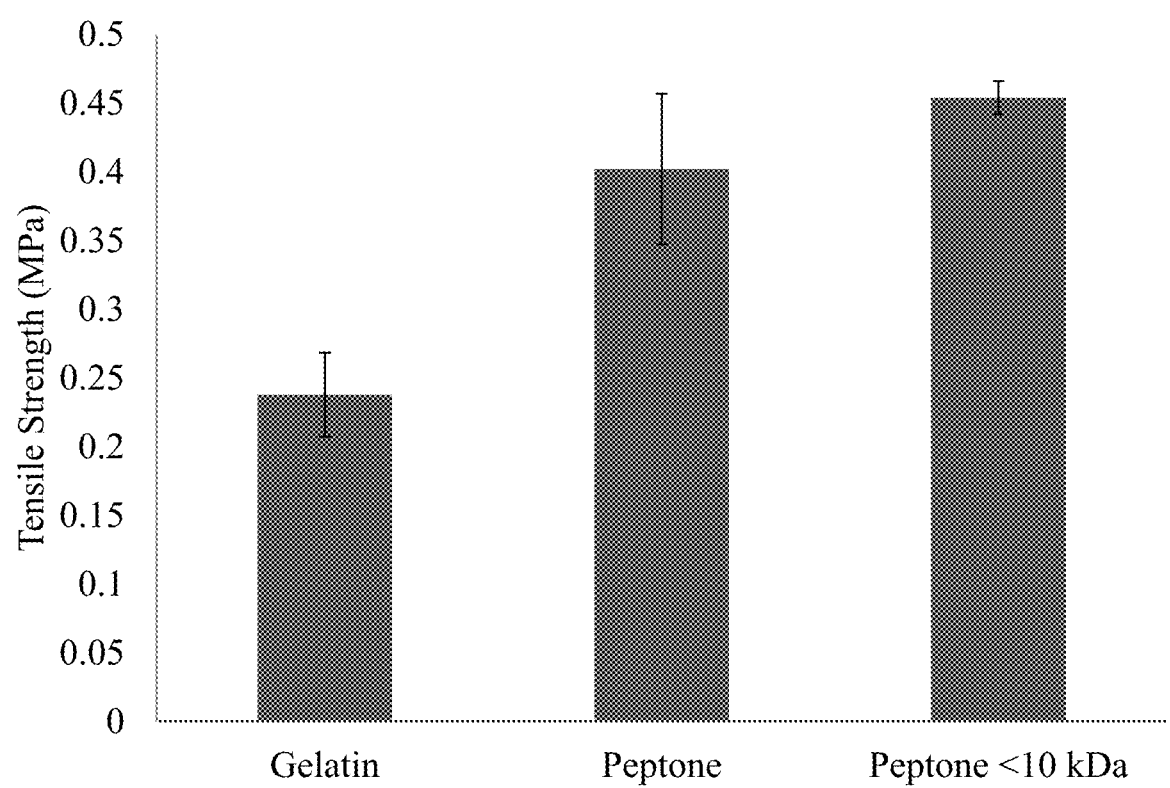
FIG. 9 shows the effect of peptone peptide size on tensile strength of foams prepared from full-length gelatin, from peptone derived from enzymatic hydrolysis of full-length gelatin and from peptone derived from enzymatic hydrolysis of full-length gelatin having peptides of less than about 10 kDa.

As shown in FIG. 9, foam prepared from a solution of peptone comprising only peptides of length less than 10 kDa required greater force for compression. Admixing the full length protein with enzymatically hydrolyzed peptides decreased the required compression force. Interestingly the mixtures resulted in lower compression force as compared to the homogenous solutions of either the full length or the enzymatically hydrolyzed solutions.

Example 9

Effect on Tensile Strength of Mixing Peptones with Full-Length Protein

5% aqueous solutions of full-length gelatin and of peptone obtained by enzymatic hydrolysis of full-length gelatin were prepared.

Samples comprising a mixture of full-length gelatin and peptone, in ratios of gelatin: peptone 40:60 and 95:5 were also prepared.

Foams were prepared from 5 mL of each of full-length gelatin, peptone alone, and gelatin: peptone mixtures at each of the two ratios, as described in Example 1. Force required for compression of each foam was tested in quadruplicates as described in Example 1. Results are presented in FIG. 10.

Figure 10:
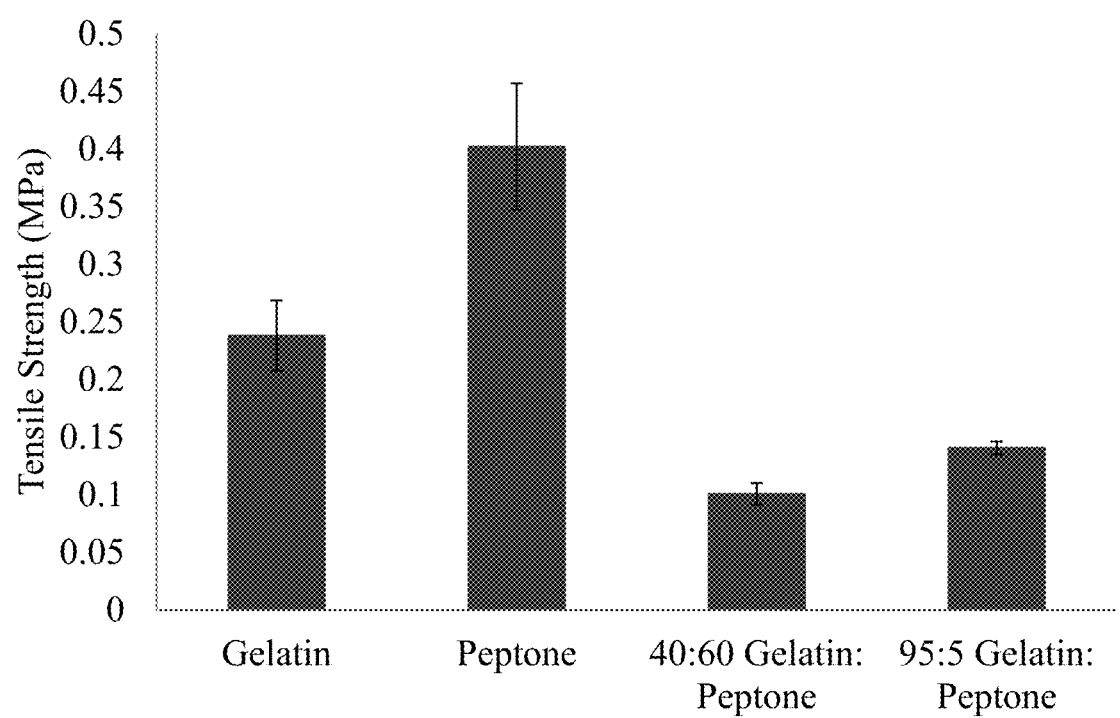
FIG. 10 shows the effect of mixing peptones obtained by enzymatic hydrolysis of full-length gelatin with full-length gelatin on the tensile strength of the foam.

As seen in FIG. 10, foams prepared from solutions comprising an admixture of full-length gelatin with peptone obtained by enzymatic hydrolysis of full-length gelatin required less force for compression than foams comprising either full-length gelatin or peptone alone.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the scope of the appended claims.

Citation or identification of any reference in this application shall not be construed as an admission that such reference is available as prior art to the invention.

The invention claimed is:

1. A method for preparing a pharmaceutical foam composition, comprising a step of: foaming a solution of a peptone with a gas,
   (i) the solution of the peptone prepared by enzymatic hydrolysis of a full-length protein in an aqueous solution,
   (ii) wherein said solution of the peptone is free of said full-length protein, (iii) wherein the peptone is present at a concentration of at least 5% to less than about 50% w/v of the solution: and wherein the method further comprises adding fibrinogen to said solution of said peptone, prior to said foaming.

* * * * *